United States Patent
Ryu et al.

(10) Patent No.: US 10,702,241 B2
(45) Date of Patent: Jul. 7, 2020

(54) PORTABLE ULTRASONIC DIAGNOSTIC DEVICE AND POWER EFFICIENCY IMPROVEMENT METHOD THEREIN

(71) Applicant: HEALCERION CO., LTD., Seoul (KR)

(72) Inventors: Jeong Won Ryu, Seoul (KR); You Chan Choung, Seoul (KR); Wook Jin Chung, Seoul (KR)

(73) Assignee: HEALCERION CO., LTD., Seoul (KR)

(*) Notice: Subject to any disclaimer, the term of this patent is extended or adjusted under 35 U.S.C. 154(b) by 592 days.

(21) Appl. No.: 15/324,097

(22) PCT Filed: Mar. 13, 2015

(86) PCT No.: PCT/KR2015/002450
§ 371 (c)(1),
(2) Date: Jan. 5, 2017

(87) PCT Pub. No.: WO2016/006790
PCT Pub. Date: Jan. 14, 2016

(65) Prior Publication Data
US 2017/0156693 A1 Jun. 8, 2017

(30) Foreign Application Priority Data
Jul. 8, 2014 (KR) .................. 10-2014-0085249

(51) Int. Cl.
*A61B 8/08* (2006.01)
*A61B 8/00* (2006.01)
*A61B 8/14* (2006.01)

(52) U.S. Cl.
CPC ............. *A61B 8/4427* (2013.01); *A61B 8/08* (2013.01); *A61B 8/14* (2013.01); *A61B 8/4483* (2013.01);
(Continued)

(58) Field of Classification Search
CPC .......... A61B 8/4427; A61B 8/08; A61B 8/14; A61B 8/4483; A61B 8/56; A61B 8/585
See application file for complete search history.

(56) References Cited

U.S. PATENT DOCUMENTS

| 4,016,750 A | * | 4/1977 | Green | ................ A61B 8/08 73/629 |
| 4,016,862 A | * | 4/1977 | Lancee | ............... G01N 29/40 600/443 |

(Continued)

FOREIGN PATENT DOCUMENTS

| JP | 1995-236640 | 9/1995 | ............... A61B 8/00 |
| JP | 2006-141465 | 6/2006 | ............... A61B 8/00 |

(Continued)

OTHER PUBLICATIONS

International Search Report (ISR) dated May 4, 2015 in PCT/KR2015/002450 with English translation.

*Primary Examiner* — Joanne M Hoffman
(74) *Attorney, Agent, or Firm* — Harness, Dickey & Pierce, P.L.C.

(57) ABSTRACT

A portable ultrasonic diagnostic device according to the present invention comprises: a measurement depth setting unit for setting the measurement depth intended to be measured; a voltage supply unit for supplying the voltage to be applied to a pulse generation unit depending on the set measurement depth, wherein the smaller the set measurement depth, the smaller the voltage supplied; and a pulse generation unit for generating the electrical pulse to be applied to an ultrasonic transducer in order to generate ultrasonic wave, wherein the generated electrical pulse is an electrical pulse of a voltage corresponding to the voltage supplied from the voltage supply unit.

4 Claims, 9 Drawing Sheets

(52) U.S. Cl.
CPC ............... *A61B 8/56* (2013.01); *A61B 8/585* (2013.01); *A61B 8/54* (2013.01)

(56) References Cited

U.S. PATENT DOCUMENTS

| | | | | |
|---|---|---|---|---|
| 4,111,054 A | * | 9/1978 | Jorgensen | A61B 8/0866 |
| | | | | 73/611 |
| 4,416,286 A | * | 11/1983 | Iinuma | A61B 8/06 |
| | | | | 600/441 |
| 4,472,972 A | * | 9/1984 | Riley | G01S 7/52023 |
| | | | | 73/620 |
| 4,476,874 A | * | 10/1984 | Taenzer | A61B 8/06 |
| | | | | 600/441 |
| 4,819,652 A | * | 4/1989 | Micco | A61B 8/06 |
| | | | | 600/455 |
| 5,113,706 A | * | 5/1992 | Pittaro | A61B 8/4483 |
| | | | | 600/447 |
| 5,313,947 A | * | 5/1994 | Micco | A61B 8/06 |
| | | | | 600/455 |
| 5,477,858 A | * | 12/1995 | Norris | G01S 7/52033 |
| | | | | 600/441 |
| 6,186,950 B1 | * | 2/2001 | Averkiou | A61B 8/06 |
| | | | | 600/440 |
| 2001/0034484 A1 | * | 10/2001 | Nakamura | A61B 8/14 |
| | | | | 600/443 |
| 2002/0173721 A1 | * | 11/2002 | Grunwald | A61B 8/00 |
| | | | | 600/437 |
| 2005/0277835 A1 | * | 12/2005 | Angelsen | A61B 8/14 |
| | | | | 600/437 |
| 2007/0016023 A1 | * | 1/2007 | Phelps | G01S 7/52023 |
| | | | | 600/437 |
| 2008/0208045 A1 | * | 8/2008 | Rielly | A61B 8/00 |
| | | | | 600/437 |
| 2013/0137982 A1 | * | 5/2013 | Lee | A61B 8/5207 |
| | | | | 600/443 |
| 2013/0319123 A1 | * | 12/2013 | Wang | G01N 29/2418 |
| | | | | 73/655 |
| 2014/0276069 A1 | * | 9/2014 | Amble | A61B 8/5207 |
| | | | | 600/447 |
| 2016/0074017 A1 | * | 3/2016 | Lee | A61B 8/54 |
| | | | | 600/442 |

FOREIGN PATENT DOCUMENTS

| | | | | |
|---|---|---|---|---|
| JP | 2007-275354 | | 10/2007 | ............... A61B 8/00 |
| KR | 10-2009-0111552 | | 10/2009 | ............... A61B 8/00 |

* cited by examiner

| MEASUREMENT DEPTH (cm) | VOLTAGE (V) |
|---|---|
| 3 | 15 |
| 4 | 20 |
| 5 | 25 |
| 6 | 30 |
| 7 | 35 |
| 8 | 40 |
| 9 | 45 |
| 10 | 50 |
| 11 | 55 |
| 12 | 60 |
| 13 | 65 |
| 14 | 70 |
| 15 | 75 |
| 16 | 80 |
| 17 | 85 |
| 18 | 90 |
| 19 | 95 |
| 20 | 100 |

PORTABLE ULTRASONIC DIAGNOSTIC DEVICE AND POWER EFFICIENCY IMPROVEMENT METHOD THEREIN

CROSS-REFERENCE TO RELATED APPLICATIONS

This application is a national phase application of PCT Application No. PCT/KR2015/002450, filed on 13 Mar. 2015, which claims benefit of Korean Patent Application 10-2014-0085249, filed on 8 Jul. 2014. The entire disclosure of the applications identified in this paragraph are incorporated herein by reference.

FIELD

The present invention relates to a portable ultrasonic diagnostic apparatus, and more particularly, to a portable ultrasonic apparatus and a method of improving power efficiency of the ultrasonic diagnostic apparatus.

BACKGROUND

With noninvasive and nondestructive properties, an ultrasonic diagnostic apparatus is generally used in the medical field to obtain information of the inside of a subject. Since it is possible to provide a high-resolution image of internal organs of the subject to a doctor with no surgical operations of directly incising and observing the subject, ultrasonic diagnostic systems are very importantly used in the medical field.

An ultrasonic diagnostic apparatus is a system which transmits an ultrasonic signal from a body surface of a subject toward a target portion inside the subject, extracts information from a reflected ultrasonic signal, and obtains an image of a section of soft tissue or a blood flow in a noninvasive manner.

Compared with other imaging diagnostic apparatuses such as an X-ray inspection apparatus, a computerized tomography (CT) scanner, a magnetic resonance image (MRI) scanner, and a nuclear medicine inspection apparatus, since having a small size, being cheap, being capable of displaying in real time, and having excellent safety without being exposed to X-rays, such ultrasonic diagnostic system described above is generally used to diagnose hearts, internal organs in an abdominal cavity, urinary systems, and genital organs.

Due to an alternating current (AC) power source to which power is constantly supplied, a power shortage does not occur in a typical ultrasonic diagnostic apparatus. However, recently, as portable ultrasonic diagnostic apparatuses using batteries with limited power as power sources have been used, technologies for providing a maximum amount of usage time by minimum power are needed.

DISCLOSURE OF INVENTION

Technical Problem

Existing portable ultrasonic diagnostic apparatuses generate pulse signals with maximum voltages which are uniform regardless of depths for measurement and use pulse signals with the same maximum voltages when measurement is performed at shallower depths. Due to this, since high loads are applied to a battery end and a circuit portion, power efficiency is not high.

Therefore, it is an aspect of the present invention to provide a portable ultrasonic diagnostic apparatus capable of improving power efficiency by adjusting a voltage of a pulse signal depending on a depth for measurement and a method of improving power efficiency of the portable ultrasonic diagnostic apparatus.

Technical Solution

One aspect of the present invention provides a portable ultrasonic diagnostic apparatus including a measurement depth setting portion configured to set a measurement depth for measurement, a voltage supplying portion configured to supply a voltage to be applied to a pulse generating portion according to the set measurement depth and supply a lower voltage as the set measurement depth gets shallower, and the pulse generating portion configured to generate an electric pulse to be applied to an ultrasonic transducer to generate an ultrasonic wave and generate an electric pulse of a voltage corresponding to a voltage supplied from the voltage supplying portion.

The portable ultrasonic diagnostic apparatus may further include a variable gain amplifier configured to compensate for attenuation according to a reflection depth by amplifying an echo signal input from the ultrasonic transducer.

The portable ultrasonic diagnostic apparatus may further include a compensation property adjusting portion configured to adjust amplification properties of the variable gain amplifier according to a reflection depth.

The amplification properties may allow a gain to have a certain maximum value at the set measurement depth and have a greater value as the reflection depth is deeper within a range below the set measurement depth. Here, the amplification properties may have a form in which the gain is increased according to the reflection depth within the range below the set measurement depth.

Another aspect of the present invention provides a method of improving power efficiency of a portable ultrasonic diagnostic apparatus, including setting a measurement depth for measurement, supplying a voltage to a pulse generating portion which generates an electric pulse to be applied to an ultrasonic transducer according to the set measurement depth in which a lower voltage is supplied when the set measurement depth is shallower, and generating an electric pulse, by the pulse generating portion, according to the supplied voltage.

The method may further include compensating for attenuation according to a reflection depth by amplifying an echo signal input from the ultrasonic transducer using a variable gain amplifier.

The method may further include adjusting amplification properties of the variable gain amplifier according to a reflection depth according to the set measurement depth.

The adjusting may include adjusting amplification properties to allow a gain to have a certain maximum value at the set measurement depth and have a greater value as the reflection depth is deeper within a range below the set measurement depth. Here, the amplification properties may have a form in which the gain is increased according to the reflection depth within the range below the set measurement depth.

Advantageous Effects

According to the present invention, there is provided an effect of providing power efficiency by adjusting a voltage of a pulse signal according to a depth for measurement.

MODE FOR INVENTION

Hereinafter, exemplary embodiments of the present invention will be described in detail with reference to the drawings. In the following description and attached drawings, substantially identical components will be referred to as identical reference numerals and a repeated description thereof will be omitted. Also, in the description of the embodiments of the present invention, detailed explanations of well-known functions and components of the related art will be omitted when it is deemed that they may unnecessarily obscure the essence of the present invention.

Figure 1:
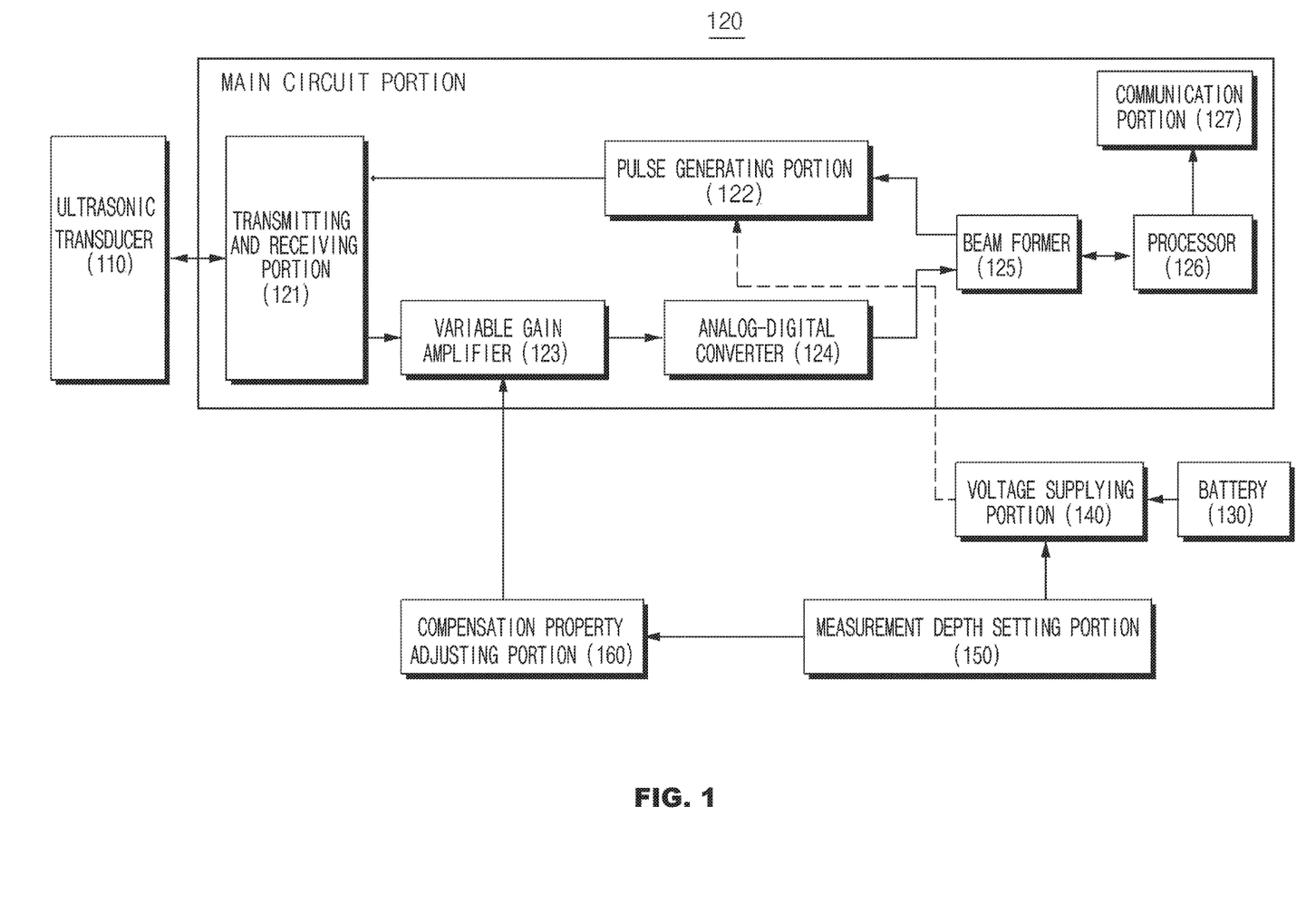
FIG. 1 illustrates a configuration of a portable ultrasonic diagnostic apparatus according to one embodiment of the present invention.

FIG. 1 illustrates a configuration of a portable ultrasonic diagnostic apparatus according to one embodiment of the present invention. The portable ultrasonic diagnostic apparatus according to the embodiment includes an ultrasonic transducer 110, a main circuit portion 120, a battery 130, a measurement depth setting portion 150, and a compensation property adjusting portion 160.

The ultrasonic transducer 110 generates an ultrasonic pulse from an electric pulse applied from the main circuit portion 120 to inspect the inside of a subject, converts an ultrasonic echo signal which is reflected by the subject and returns into an electric signal, and transfers the electric signal to the main circuit portion 120. The ultrasonic transducer 110 may be formed of a piezoelectric element array module. The piezoelectric element array module may be configured to allow a large number, such as 64, 128, 192 and the like, of piezoelectric elements to be arranged in an array shape. As the piezoelectric elements, lead zirconate titanate (PZT) with high efficiency of electro-acoustic conversion may be used. As a voltage of an electric pulse for driving a piezoelectric element, a voltage of +100 V to −100 V may be used.

The main circuit portion 120 performs functions of generating an electric pulse to be applied to the ultrasonic transducer 110, generating an ultrasonic image by analyzing an echo signal received through the ultrasonic transducer 110, and transmitting the ultrasonic image to an external display device (not shown).

In detail, the main circuit portion 120 includes a transmitting and receiving portion 121, a pulse generating portion 122, a variable gain amplifier 123, an analog-digital (A/D) converter 124, a beam former 125, a processor 126, and a communication portion 127.

The transmitting and receiving portion 121 transmits an electric pulse generated by the pulse generating portion 122 to the ultrasonic transducer 110 and transmits an echo signal received through the ultrasonic transducer 110 to the variable gain amplifier 123. For example, the transmitting and receiving portion 121 may be formed of a switch configured to connect a TX circuit and the piezoelectric element array module when transmitting ultrasonic waves and to connect an RX circuit and the piezoelectric element array module when receiving ultrasonic echoes.

The pulse generating portion 122 generates electric pulses to be applied to the ultrasonic transducer 110 for generating ultrasonic waves. Here, the pulse generating portion 122 generates electric pulses with voltages corresponding to voltages supplied from a voltage supplying portion 140 that will be described below.

The variable gain amplifier 123 amplifies echo signals input from the ultrasonic transducer 110 and compensates for attenuation of the echo signals according to reflection depths. Since ultrasonic waves are absorbed into a human body due to properties thereof, signals that are reflected from a deep place and arrive late lose more energy in such a way that size thereof is reduced. Accordingly, as a reflection depth becomes deeper (that is, as an arrival time is later), echo signals should be compensated with larger values. Accordingly, the amplification properties of the variable gain amplifier 123 according to the reflection depth may have a form that is increased according to a reflection depth or arrival time of a signal.

The A/D converter 124 converts an echo signal compensated for loss thereof by the variable gain amplifier 123 into a digital signal.

The beam former 125 performs TX beam forming and RX beam forming. TX beam forming is allowing the pulse generating portion 122 to generate adequate electric pulses using a parameter corresponding to the ultrasonic transducer 110, and for example, is delaying times of electric pulses depending on positions of piezoelectric elements to concentrate energy of ultrasonic waves on a focus at a certain distance when the ultrasonic waves are transmitted. RX beam forming is data-converting digital signals from the A/D converter 124 to be adequate for the ultrasonic transducer 110 transferring the data-converted digital signals to the processor 126, and for example, is time-delaying electric signals from piezoelectric elements according to positions and receiving times of the piezoelectric elements when ultrasonic echoes are received and generating ultrasonic data (scan data) by summing the time-delayed signals.

The processor 126 controls the beam former 125 to perform adequate beam forming at the ultrasonic transducer, generates an ultrasonic image using the scan data to transmit the ultrasonic image to an external display device through the communication portion 127 or transmits the scan data to the external display device through the communication portion 127, and controls each of the components of the portable ultrasonic diagnostic apparatus. The processor 126 may compress the scan data to reduce a bandwidth used for communication as necessary.

The communication portion 127 may use a wired or wireless communication type communication module for transmitting and receiving data with the external display device. The wired communication type may include a wired with cable such as a universal serial bus (USB) cable and the like. The wireless communication type may include one of Bluetooth, wireless USB, wireless local area network (LAN), wireless fidelity (WiFi), Zigbee, and Infrared data association (IrDA).

The external display device configured to display an ultrasonic image using the ultrasonic image or the scan data transmitted through the communication portion 127 may be, for example, a personal computer (PC), a smart phone, a table PC, personal digital assistants (PDA) and the like.

According to the embodiment, the portable ultrasonic diagnostic apparatus may include a display portion (not shown) thereof for displaying the ultrasonic image generated by the processor 126. In this case, the communication portion 127 configured to transmit ultrasonic images or scan data to the outside may be not provided.

The battery 130 supplies power for operations of the portable ultrasonic diagnostic apparatus, including power necessary for the pulse generating portion 122 to generate electric pulses.

Generally, since a uniform maximum voltage (for example, 100 V) is supplied to the pulse generating portion 122 regardless of a measurement depth, the pulse generating portion 122 generates electric pulse signals with uniform maximum voltages (for example, a peak to peak value of +100 V to −100 V). However, in the embodiment of the present invention, a measurement depth for measurement is set and a voltage adjusted according to the set measurement depth is supplied to the pulse generating portion 122, thereby improving power efficiency. When the measurement depth for measurement is determined, since data at a position deeper than the measurement depth is actually unnecessary, it is unnecessary to supply maximum voltage.

The measurement depth setting portion 150 sets a measurement depth for measuring a subject. The measurement depth may be received from a user. The portable ultrasonic diagnostic apparatus may include a user interface for inputting the measurement depth. Depending on the embodiments, when the user inputs a portion for diagnosis, symptom, or purpose, a measurement depth may be set according to predetermined references corresponding thereto.

The voltage supplying portion 140 generates a voltage according to a measurement depth set by the measurement depth setting portion 150 and supplies the voltage to the pulse generating portion 122. Here, the voltage supplying portion 140 supplies a lower voltage as a measurement depth is shallower and supplies a higher voltage as a measurement depth is deeper. For example, a direct current (DC)-DC converter may be used as the voltage supplying portion 140. In this case, supplied voltages may be adjusted by modulating pulse widths by the DC-DC converter. According to the embodiment of the present invention, since the pulse generating portion 122 does not always supply uniform maximum voltage but supplies voltages lower than the maximum voltage according to set measurement depths, loads applied to a battery end and a circuit portion become reduced, thereby increasing power efficiency.

Figure 2:
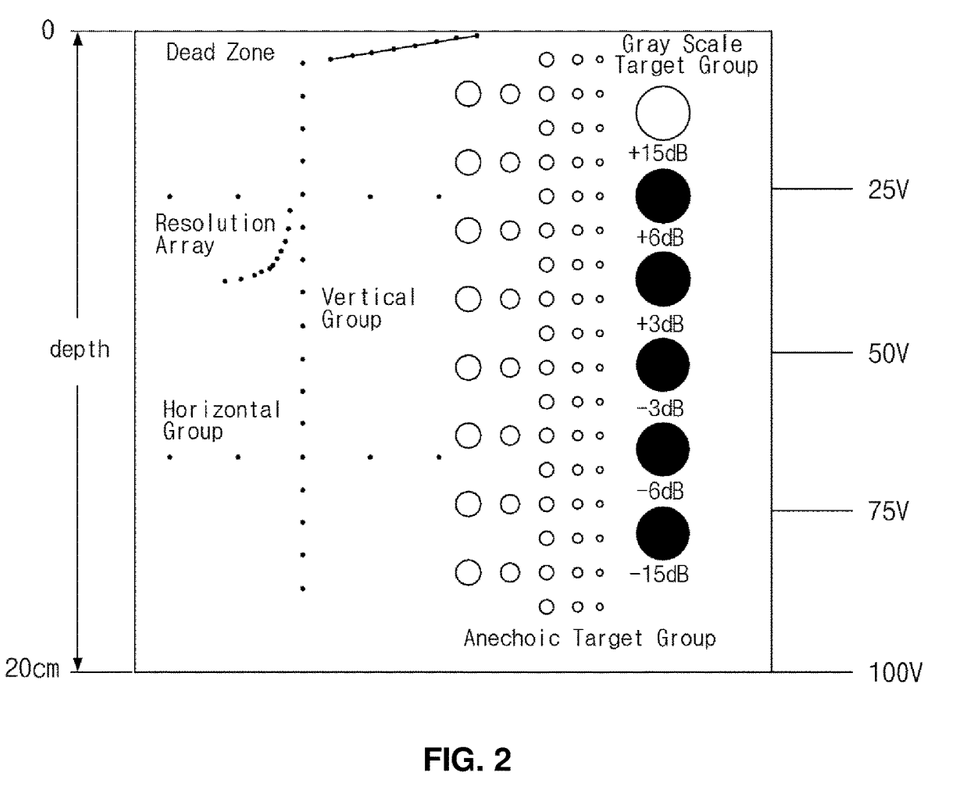
FIG. 2 illustrates an example of a phantom that is measurable instead of a human body and displayed with supplied voltages according to measurement depths.

FIG. 2 illustrates an example of a phantom that is measurable instead of a human body and displayed with supplied voltages according to measurement depths. Referring to FIG. 2, when a maximum measurement depth is 20 cm and a set measurement depth is 20 cm that is the maximum measurement depth, a maximum voltage of 100 V is supplied. However, when a set measurement depth is shallower than 20 cm, a voltage of 75 V, 50 V, or 25 V is supplied as shown in the drawing.

Figure 3:
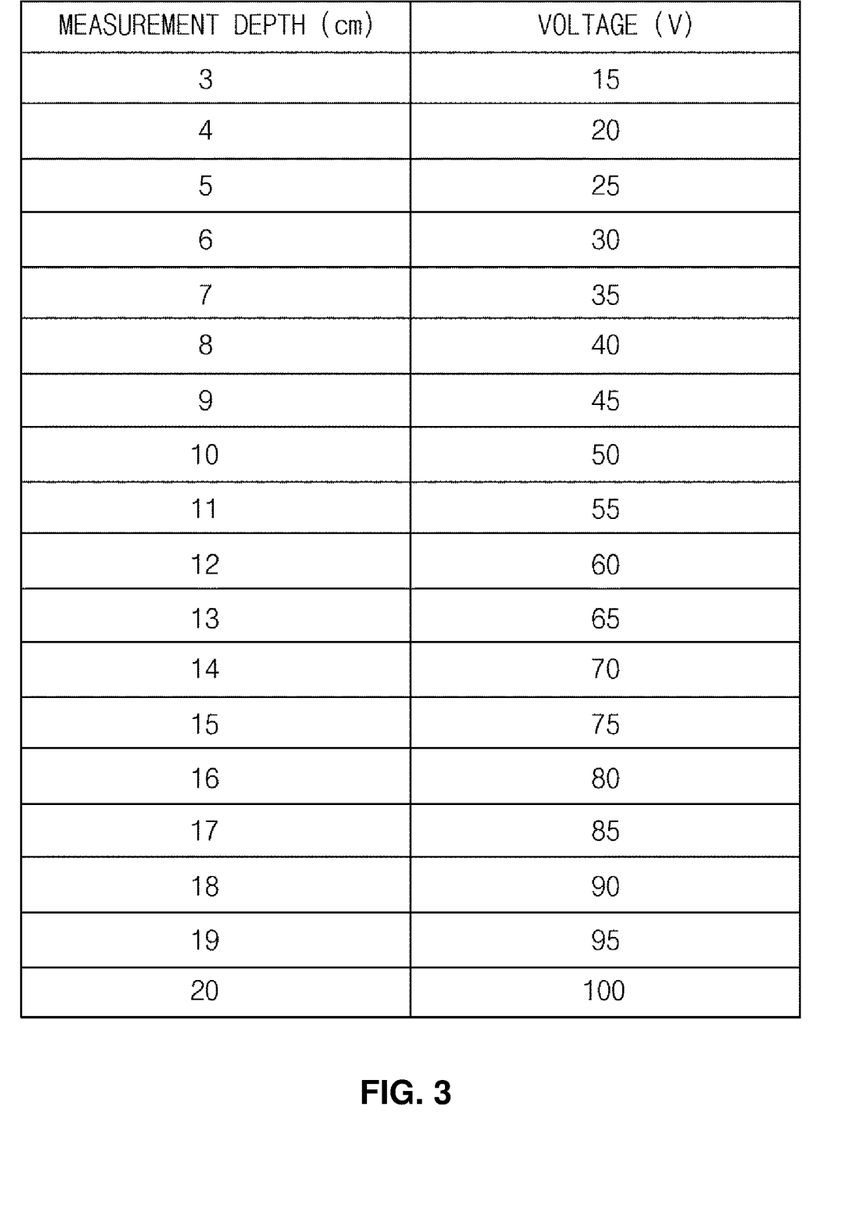
FIG. 3 illustrates one example of a measurement depth-voltage table.

To allow the voltage supplying portion 140 to supply a voltage adjusted according to a set measurement depth, a measurement depth-voltage table that indicates voltages according to measurement depths in a memory (not shown) of the portable ultrasonic diagnostic apparatus. The processor 126 controls the voltage supplying portion 140 by referring to the measurement depth-voltage table, thereby adjusting supplied voltages. FIG. 3 illustrates one example of the measurement depth-voltage table described above. Referring to FIG. 3, supplied voltages corresponding to measurement depths 3 cm to 20 cm are shown. Here, excluding of 1 to 2 cm is because interesting areas in an ultrasonic image are generally places positioned at depths of 3 cm or below from the skin of a human body. Since areas at depths of 1 to 2 cm are mainly subcutaneous fat including skin, they do not have significant information for clinical diagnosis.

Referring to FIG. 1 again, the pulse generating portion 122 generates electric pulses with voltages corresponding to voltages supplied from the voltage supplying portion 140. For example, the pulse generating portion 122 generates electric pulse signals with a peak to peak value of +100 V to −100 V when a voltage of 100 V is supplied from the voltage supplying portion 140 and generates electric pulse signals with a peak to peak value of +50 V to 50 V when a voltage of 50 V is supplied.

When the pulse generating portion 122 generates electric pulse signals of different voltages depending on set measurement depths as described above, a level of an ultrasonic signal emitted to a subject through the ultrasonic transducer 110 is changed. Accordingly, a level of an echo signal input from the ultrasonic transducer 110 is also changed.

Figure 4:
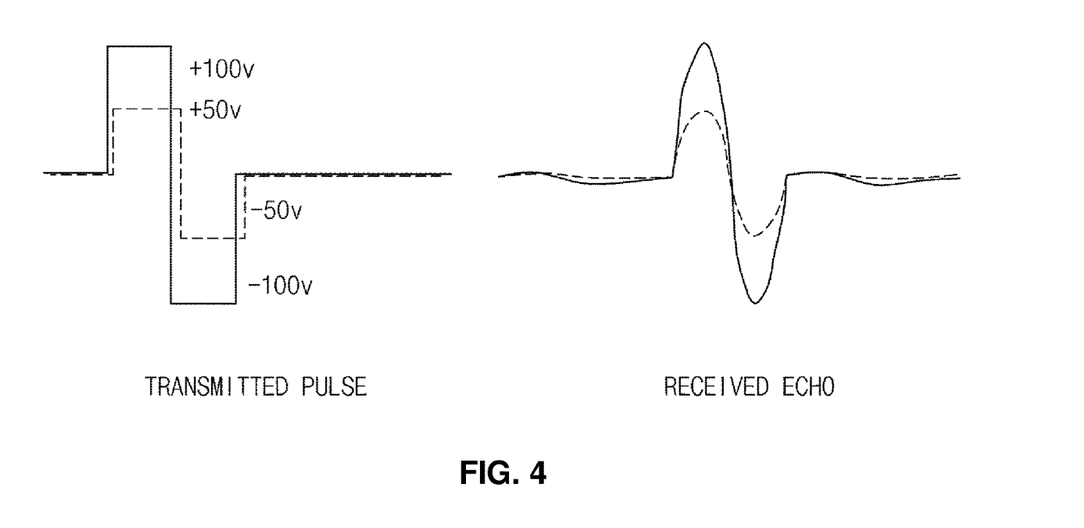
FIG. 4 illustrates electric pulses with different voltages generated by a pulse generating portion 122 and echo signals according thereto.

FIG. 4 illustrates electric pulses with different voltages generated by the pulse generating portion 122 and echo signals according thereto. Referring to FIG. 4, when a voltage of an electric pulse is reduced, a level of an echo signal according thereto is also reduced. Accordingly, it is necessary to compensate for the reduced level of the echo signal as described above.

For this, in the embodiment of the present invention, amplification properties according to a reflection depth of the variable gain amplifier 123 are allowed to be adjusted according to a measurement depth set by the measurement depth setting portion 150. Referring to FIG. 1, the compensation property adjusting portion 160 adjusts amplification properties according to the reflection depth (that is, an arrival time of a signal) of the variable gain amplifier 123 depending on a measurement depth set through the measurement depth setting portion 150. Adjusting of the amplification properties of the variable gain amplifier 123 may be, for example, achieved by configuring some of elements forming the variable gain amplifier 123 with variable elements and adequately adjusting element values of variable elements. Although the compensation property adjusting portion 160 is shown as a separate component from the variable gain amplifier 123 in FIG. 1, the compensation property adjusting portion 160 may be a component included in the variable gain amplifier 123.

Figure 5:
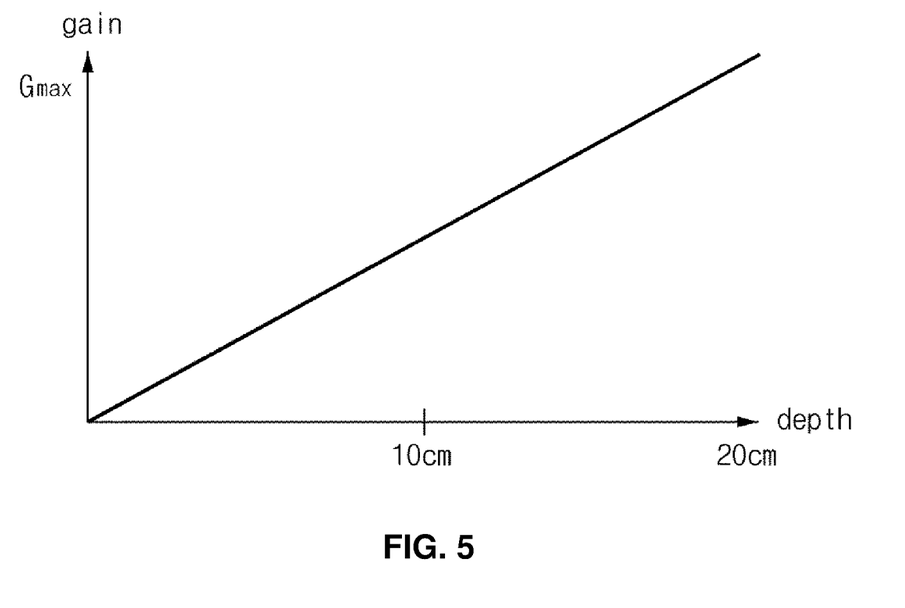
FIG. 5 is a graph illustrating an example of amplification properties according to a reflection depth of a variable gain amplifier 123.

FIG. 5 is a graph illustrating an example of the amplification properties of the variable gain amplifier 123 according to the reflection depth when a uniform maximum voltage (for example, 100 V) is supplied to the pulse generating portion 122 regardless of measurement depth. Referring to FIG. 5, the amplification properties have a maximum gain Gmax at a maximum depth of 20 cm and have a form in which a gain is linearly increased according to reflection depth. Although it is shown as an example that the gain is linearly increased according to the reflection depth in FIG. 5, the gain may be increased like an exponential function or a logarithmic function according to attenuation properties in a human body.

Figure 6:
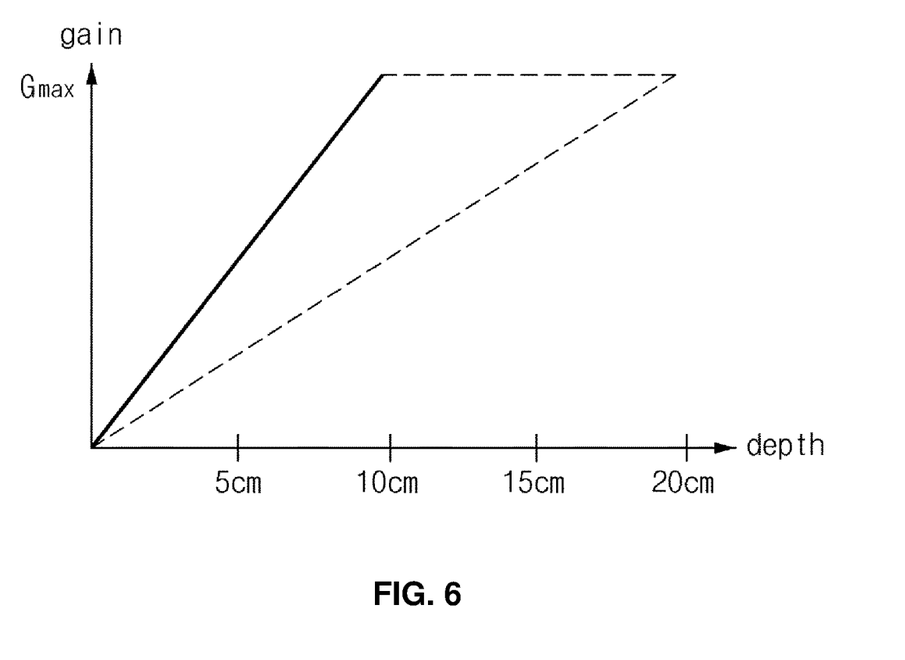
FIG. 6 is a graph which illustrates amplification properties adjusted according to a reflection depth of the variable gain amplifier 123 according to embodiments of the present invention and illustrates amplification properties when a measurement depth is 10 cm.
Figure 7:
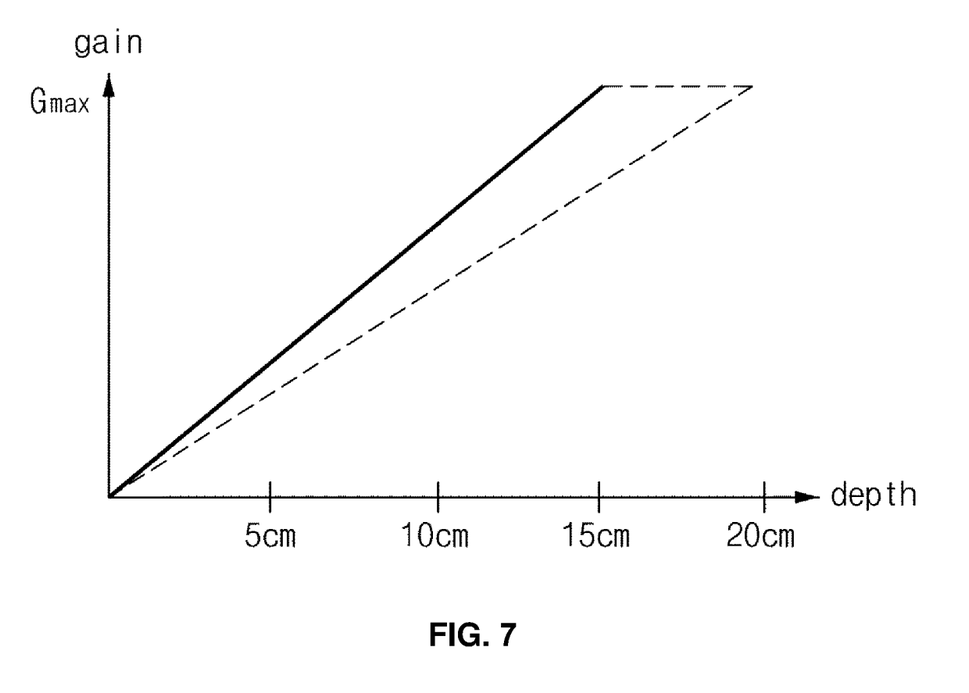
FIG. 7 is a graph which illustrates amplification properties adjusted according to a reflection depth of the variable gain amplifier 123 according to embodiments of the present invention and illustrates amplification properties when a measurement depth is 15 cm.
Figure 8:
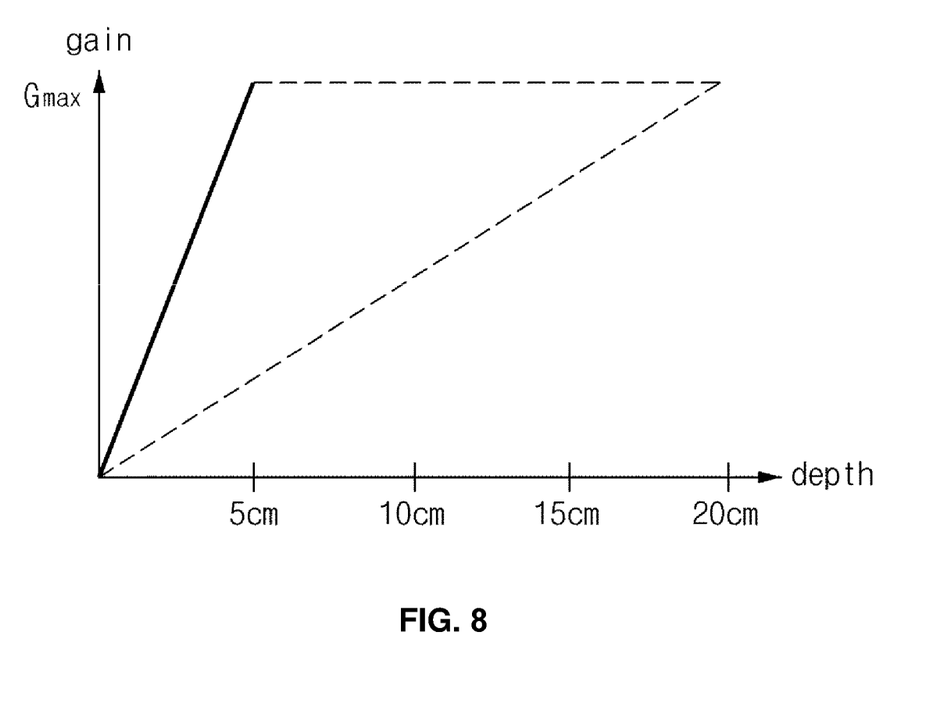
FIG. 8 is a graph which illustrates amplification properties adjusted according to a reflection depth of the variable gain amplifier 123 according to embodiments of the present invention and illustrates amplification properties when a measurement depth is 5 cm.

In the embodiment of the present invention, to compensate for a level of an echo signal that is reduced as a voltage of an electric pulse generated by the pulse generating portion 122 is reduced, the amplification properties of the variable gain amplifier 123 according to the reflection depth may be adjusted, for example, as shown in FIGS. 6 to 8. FIGS. 6, 7, and 8 illustrate amplification properties when set measurement depths are 10 cm, 15 cm, and 5 cm, respectively.

Referring to FIGS. 6 to 8, amplification properties are adjusted to have a maximum gain Gmax at a set measurement depth and have a greater gain when a reflection depth is deeper within a range below a set measurement depth, that is, to allow a gain to be gradually increased according to a reflection depth within a range below a measurement depth and have the maximum gain Gmax at the set measurement depth.

Referring to FIG. 6, the amplification properties have a maximum gain Gmax at a set measurement depth of 10 cm and have a form in which a gain is gradually increased according to a reflection depth within a range below 10 cm.

Referring to FIG. 3, a voltage of an electric pulse generated by the pulse generating portion 122 is a peak to peak value of +100 V to −100 V when the set measurement depth is 20 cm and an echo signal reflected at the reflection depth of 10 cm is amplified with a gain of ½ Gmax through the variable gain amplifier 123. Since the voltage generated by the pulse generating portion 122 is reduced to be with a peak to peak value of +50 V to −50 V when the set measurement depth is 10 cm, a level of the echo signal is reduced to half. However, since the gain at the reflection depth of 10 cm is the maximum gain Gmax according to adjustment of the amplification properties, the level of the echo signal amplified by the variable gain amplifier 123 is identical to a case in which a voltage of an electric pulse is a peak to peak value of +100 V to −100 V.

Referring to FIG. 7, the amplification properties have a maximum gain Gmax at a set measurement depth of 15 cm and have a form in which a gain is gradually increased according to a reflection depth within a range below 15 cm.

Referring to FIG. 3, a voltage of an electric pulse generated by the pulse generating portion 122 is a peak to peak value of +100 V to −100 V when the set measurement depth is 20 cm and an echo signal reflected at the reflection depth of 15 cm is amplified with a gain of ¾ Gmax through the variable gain amplifier 123. Since the voltage generated by the pulse generating portion 122 is reduced to be with a peak to peak value of +75V to −75V when the set measurement depth is 15 cm, a level of the echo signal is reduced to 75%. However, since the gain at the reflection depth of 15 cm is the maximum gain Gmax according to adjustment of the amplification properties, the level of the echo signal amplified by the variable gain amplifier 123 is identical to a case in which a voltage of an electric pulse is a peak to peak value of +100 V to −100 V.

Referring to FIG. 8, the amplification properties have a maximum gain Gmax at a set measurement depth of 5 cm and have a form in which a gain is gradually increased according to a reflection depth within a range below 5 cm.

Referring to FIG. 3, a voltage of an electric pulse generated by the pulse generating portion 122 is a peak to peak value of +100 V to −100 V when the set measurement depth is 20 cm and an echo signal reflected at the reflection depth of 5 cm is amplified with a gain of ¼ Gmax through the variable gain amplifier 123. Since the voltage generated by the pulse generating portion 122 is reduced to be with a peak to peak value of +25V to −25V when the set measurement depth is 5 cm, a level of the echo signal is reduced to 25%. However, since the gain at the reflection depth of 5 cm is the maximum gain Gmax according to adjustment of the amplification properties, the level of the echo signal amplified by the variable gain amplifier 123 is identical to a case in which a voltage of an electric pulse is a peak to peak value of +100 V to −100 V.

Although it is shown as an example that the gain is linearly increased according to the reflection depth to the set measurement depth in FIGS. 6 to 8, the gain may be increased like an exponential function or a logarithmic function according to attenuation properties in a human body.

Figure 9:
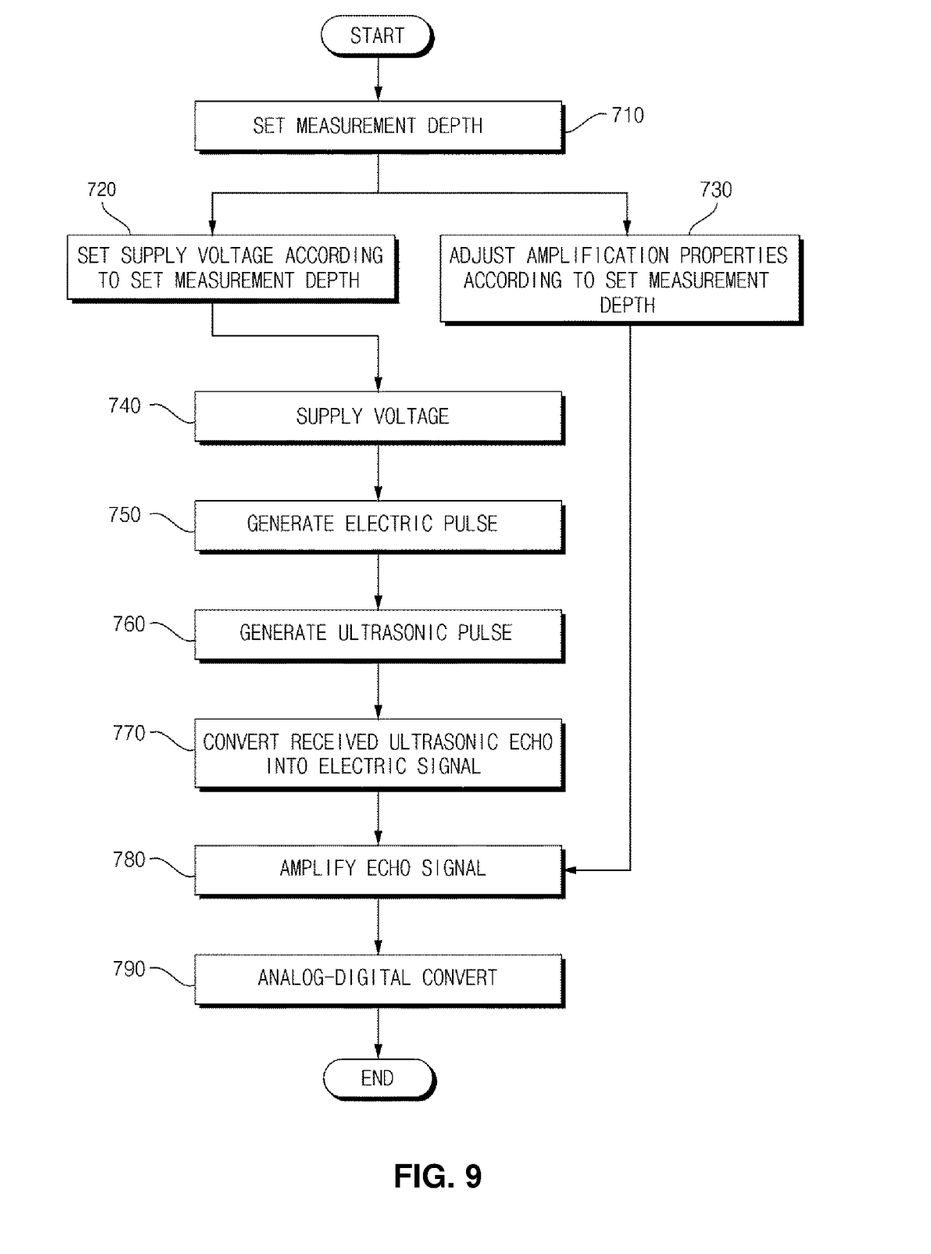
FIG. 9 is a flowchart illustrating a method of improving power efficiency of the portable ultrasonic diagnostic apparatus according to one embodiment of the present invention.

FIG. 9 is a flowchart illustrating a method of improving power efficiency of the portable ultrasonic diagnostic apparatus according to one embodiment of the present invention. The method of improving power efficiency according to the embodiment includes operations performed by the portable ultrasonic diagnostic apparatus described. Accordingly, even content omitted below but related to the portable ultrasonic diagnostic apparatus will be also applied to the method of improving power efficiency according to the embodiment.

In operation 710, the measurement depth setting portion 150 sets a measurement depth for measuring a subject.

In operation 720, the voltage supplying portion 140 sets a voltage to be supplied to the pulse generating portion 122 according to the set measurement depth.

In operation 730, the compensation property adjusting portion 160 adjusts amplification properties of the variable gain amplifier 123 according to a reflection depth according to the set measurement depth.

In operation 740, the voltage supplying portion 140 generates and supplies the set voltage to the pulse generating portion 122.

In operation 750, the pulse generating portion 122 generates an electric pulse of a voltage corresponding to the supplied voltage.

In operation 760, the ultrasonic transducer 110 generates an ultrasonic pulse from the electric pulse and emits the ultrasonic pulse to the inside of the subject.

In operation 770, the ultrasonic transducer 110 converts an ultrasonic echo reflected and received from the inside of the subject into an electric signal.

In operation 780, the variable gain amplifier 123 amplifies an echo signal that is a converted electric signal according to the amplification properties adjusted in operation 730 and compensates for attenuation according to the reflection depth.

In operation 790, the A/D converter 124 converts the echo signal compensated for loss thereof by the variable gain amplifier 123 into a digital signal.

The exemplary embodiments of the present invention have been described above. It should be understood by one of ordinary skill in the art that the present invention may be modified without departing from the essential features of the present invention. Therefore, the disclosed embodiments should be considered not in a limitative point of view but in a descriptive point of view. It should be understood that the scope of the present invention is defined by the claims not by the above description and includes all differences within the equivalent scope thereof.

What is claimed is:

1. A portable ultrasonic diagnostic apparatus comprising:
a user interface for setting a measurement depth for measurement;
a voltage supply circuit configured to supply a voltage to a pulse generator according to the set measurement depth, wherein a lower supplied voltage corresponds to a shallower set measurement depth;
a variable gain amplifier configured to compensate for attenuation according to a reflection depth by amplifying an echo signal input from an ultrasonic transducer, wherein the variable gain amplifier includes variable elements to adjust amplification properties of the variable gain amplifier according to a reflection depth, wherein the amplification properties allow a gain to have a maximum value Gmax at the set measurement depth, and the gain is gradually increased up to the maximum value Gmax as the reflection depth gets deeper from zero to the set measurement depth;
the pulse generator configured to generate an electric pulse to be applied to the ultrasonic transducer to generate an ultrasonic wave, the generated electric pulse including a voltage corresponding to the voltage supplied from the voltage supply circuit.

2. The portable ultrasonic diagnostic apparatus of claim 1, wherein the amplification properties are defined to increase the gain according to the reflection depth as the reflection depth gets deeper from zero to the set measurement depth.

3. A method of improving power efficiency of a portable ultrasonic diagnostic apparatus, the method comprising:
setting a measurement depth for measurement;
supplying a voltage to a pulse generator which generates an electric pulse to be applied to an ultrasonic transducer according to the set measurement depth, where a lower supplied voltage corresponds to a shallower set measurement depth;
compensating for attenuation according to a reflection depth by amplifying an echo signal input from the ultrasonic transducer using a variable gain amplifier;
adjusting amplification properties of the variable gain amplifier according to a reflection depth according to the set measurement depth, to allow a gain to have a maximum value Gmax at the set measurement depth, and to gradually increase the gain up to the maximum value Gmax as the reflection depth gets deeper from zero to the set measurement depth; and
generating an electric pulse, by the pulse generator, according to the supplied voltage.

4. The method of claim 3, wherein the amplification properties are defined to increase the gain according to the reflection depth as the reflection depth gets deeper from zero to the set measurement depth.

* * * * *